US012788892B2

(12) United States Patent
Hanson

(10) Patent No.: US 12,788,892 B2
(45) Date of Patent: Nov. 10, 2026

(54) ASPIRATION DEVICE INCLUDING AIR PURGE TIP

(71) Applicant: Boston Scientific Scimed, Inc., Maple Grove, MN (US)

(72) Inventor: Cass Alexander Hanson, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 975 days.

(21) Appl. No.: 18/073,186

(22) Filed: Dec. 1, 2022

(65) Prior Publication Data

US 2023/0173187 A1 Jun. 8, 2023

Related U.S. Application Data

(60) Provisional application No. 63/285,555, filed on Dec. 3, 2021.

(51) Int. Cl.

*A61M 5/31* (2006.01)
*A61M 5/315* (2006.01)
*A61M 25/00* (2006.01)

(52) U.S. Cl.

CPC ...... *A61M 5/3148* (2013.01); *A61M 5/31511* (2013.01); *A61M 25/0014* (2013.01); *A61M 2005/3142* (2013.01)

(58) Field of Classification Search

CPC ............ A61M 5/3148; A61M 5/31511; A61M 25/0014; A61M 2005/3142; A61M 1/71; A61M 25/10182; A61M 2005/31516; A61M 2025/1077; A61M 2205/073; A61M 2210/12; A61M 1/815; A61B 17/22; A61B 2017/22079; A61B 2217/005

See application file for complete search history.

(56) References Cited

U.S. PATENT DOCUMENTS

| | | | | |
|---|---|---|---|---|
| 5,195,985 A | 3/1993 | Hall | | |
| 2010/0034705 A1* | 2/2010 | Mundt | .............. | A61M 5/14216 422/400 |

(Continued)

OTHER PUBLICATIONS

FlowTriever® The First Mechanical Thrombectomy Device Indicated for Pulmonary Embolism, Inari Medical, 14 pages, https://www.inarimedical.com/flowtriever, Accessed Oct. 12, 2021.

(Continued)

*Primary Examiner* — James D Ponton
(74) *Attorney, Agent, or Firm* — SEAGER, TUFTE & WICKHEM, LLP

(57) ABSTRACT

An example syringe includes a barrel having a distal end region and an inner surface defining a lumen extending therein, wherein the inner surface includes a proximally facing surface, and wherein the distal end region includes a distal end. The syringe also includes a plunger having a body portion and a distal tip extending distally away from a distal end region of the body portion, wherein the distal end region includes a distally facing surface. Further, the plunger is configured to be positioned within the lumen of the barrel and a portion of the distal tip of the plunger extends distally of the distal end of the barrel when the plunger is positioned within the lumen of the barrel.

9 Claims, 4 Drawing Sheets

(56) References Cited

U.S. PATENT DOCUMENTS

| | | | | |
|---|---|---|---|---|
| 2014/0114284 | A1* | 4/2014 | Rowe .................... | A61M 39/20 604/513 |
| 2020/0330724 | A1 | 10/2020 | Mikhail et al. | |
| 2021/0338255 | A1 | 11/2021 | Alesi et al. | |

OTHER PUBLICATIONS

International Search Report and Written Opinion dated Mar. 28, 2023 for International Application No. PCT/US2022/051533.

* cited by examiner

ASPIRATION DEVICE INCLUDING AIR PURGE TIP

CROSS-REFERENCE TO RELATED APPLICATIONS

This application claims the benefit of priority under 35 U.S.C. § 119 of U.S. Provisional Application No. 63/285,555, filed Dec. 3, 2021, the entire disclosure of which is hereby incorporated by reference.

TECHNICAL FIELD

The present disclosure pertains to medical devices, and methods for manufacturing medical devices. More particularly, the present disclosure pertains to large bore syringes connected with other structures, and methods for manufacturing and using such devices.

BACKGROUND

A wide variety of intracorporeal medical devices have been developed for medical use, for example, intravascular use. Some of these devices include syringes, aspiration devices, thrombectomy devices, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example syringe includes a barrel having a distal end region and an inner surface defining a lumen extending therein, wherein the inner surface includes a proximally facing surface, and wherein the distal end region includes a distal end. The syringe also includes a plunger having a body portion and a distal tip extending distally away from a distal end region of the body portion, wherein the distal end region includes a distally facing surface. Further, the plunger is configured to be positioned within the lumen of the barrel and a portion of the distal tip of the plunger extends distally of the distal end of the barrel when the plunger is positioned within the lumen of the barrel.

Alternatively or additionally to any of the embodiments above, wherein the distal end region of the barrel is configured to couple to a manifold of a catheter system, and wherein a portion of the distal tip of the plunger is configured to extend into a lumen of the manifold when the barrel is coupled to the manifold.

Alternatively or additionally to any of the embodiments above, wherein the portion of the distal tip extending into the manifold is configured to purge air from the lumen of the manifold.

Alternatively or additionally to any of the embodiments above, wherein the body portion of the plunger includes a first outer diameter, and wherein the distal tip portion of the plunger includes a second outer diameter smaller than the first outer diameter.

Alternatively or additionally to any of the embodiments above, wherein the distal tip of the plunger further includes a first tip portion and a second tip portion, wherein the first tip portion includes the second outer diameter, and wherein the second tip portion includes a third outer diameter smaller than the second outer diameter.

Alternatively or additionally to any of the embodiments above, wherein the first outer diameter of the plunger is about three times as large as the second outer diameter of the first tip portion.

Alternatively or additionally to any of the embodiments above, wherein the second tip portion is positioned distal to the first tip portion.

Alternatively or additionally to any of the embodiments above, wherein the first tip portion includes a first length, and wherein the second tip portion includes a second length, and wherein the first length is about twice as long as the second length.

Alternatively or additionally to any of the embodiments above, wherein the first length of the first tip portion is longer than the first diameter of the body of the plunger.

Alternatively or additionally to any of the embodiments above, wherein the distal end region of the body portion further includes a stopper, and where the stopper is configured to seal against the inner surface of the barrel.

An example catheter aspiration system includes an aspiration catheter including a tubular member coupled to a manifold, wherein the tubular member includes a first lumen extending therein, and wherein the manifold includes a second lumen extending therein, and wherein the first lumen is in fluid communication with the second lumen. The aspiration catheter system also includes a syringe configured to be coupled to the manifold, wherein the syringe includes a barrel and a plunger, the barrel having a distal end and an inner surface defining a lumen extending therein, wherein the plunger is configured to be positioned within the lumen of the barrel, and wherein the plunger includes a body portion and a distal tip extending distally away from the body portion. Further, a portion of the distal tip of the plunger is configured to extend distally of the distal end of the barrel and into the lumen of the manifold when the syringe is coupled to the manifold.

Alternatively or additionally to any of the embodiments above, wherein the portion of the distal tip extending into the manifold is configured to purge air from the lumen of the manifold.

Alternatively or additionally to any of the embodiments above, wherein the body portion of the plunger includes a first outer diameter, and wherein the distal tip portion of the plunger includes a second outer diameter smaller than the first outer diameter.

Alternatively or additionally to any of the embodiments above, wherein the distal tip of the plunger further includes a first tip portion and a second tip portion, wherein the first tip portion includes the second outer diameter, and wherein the second tip portion includes a third outer diameter smaller than the second outer diameter.

Alternatively or additionally to any of the embodiments above, wherein the first outer diameter of the plunger is about three times as large as the second outer diameter of the first tip portion.

Alternatively or additionally to any of the embodiments above, wherein the second tip portion is positioned distal to the first tip portion.

Alternatively or additionally to any of the embodiments above, wherein the first tip portion includes a first length, and wherein the second tip portion includes a second length, and wherein the first length is about twice as long as the second length.

Alternatively or additionally to any of the embodiments above, wherein the first length of the first tip portion is longer than the first diameter of the body of the plunger.

Alternatively or additionally to any of the embodiments above, wherein a distal end region of the body portion of the plunger further includes a stopper, and where the stopper is configured to seal against the inner surface of the barrel.

An example method of removing a blood clot from a blood vessel of a patient includes advancing an aspiration catheter within the blood vessel such that a distal end of the catheter is positioned adjacent to the blood clot, and wherein the catheter includes a tubular member coupled to a manifold, wherein the tubular member includes a first lumen extending therein, and wherein the manifold includes a second lumen extending therein, and wherein the first lumen is in fluid communication with the second lumen. The method further includes attaching a syringe to the manifold, wherein the syringe includes a barrel and a plunger, the barrel having a distal end and an inner surface defining a lumen extending therein, wherein the plunger is configured to be positioned is within the lumen of the barrel, and wherein the plunger includes a body portion and a distal tip extending distally away from the body portion. The method further includes advancing the plunger into the lumen of the barrel to a position in which the distal tip of the plunger extends out of the distal end of the barrel and into the lumen of the manifold. The method further includes retracting the plunger in a proximal direction, wherein retracting the plunger generates a vacuum to aspirate at least a portion of the blood clot into the first lumen of the tubular member.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
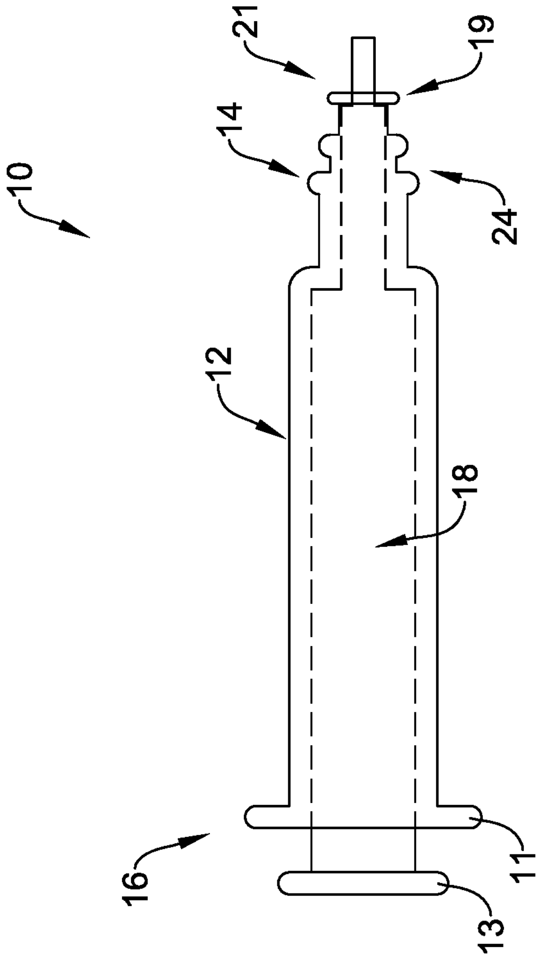
FIG. 1 illustrates an example syringe including a plunger positioned within a lumen of a barrel.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Thromboembolism may be characterized as an adverse medical condition whereby a blood clot forms an occlusion in a blood vessel. In some instances, a blood clot (thrombus) having formed in a blood vessel, dislodges and blocks another blood vessel. Blood clots in both the arterial system and the venous system may cause serious harm. For example, when an artery is occluded by a thrombus, tissue ischemia may develop. The ischemia may eventually progress to tissue infarction if the occlusion persists. Similarly, in the venous system, thrombus may also cause serious harm. For is example, thrombus may develop in the veins of the legs, a condition known as deep venous thrombosis (DVT). DVT can obstruct the flow of venous blood from the legs, thereby leading to adverse conditions such as swelling and infection. Additionally, in some instances a blood clot in the legs may break loose, travel through the bloodstream to the lungs and cause a sudden blockage in a lung artery, a condition known as a pulmonary embolism. Pulmonary embolism can lead to permanent damage to the lungs, low oxygen levels in the blood and damage to other organs due to the lack of oxygen.

However, it can be appreciated that the re-establishment of sufficient blood flow may significantly reduce harm caused by thromboembolism. A variety of medical treatments exist to re-establish blood flow through an occluded vessel. For example, in some instance medicines which include anticoagulants may be utilized to prevent the blood clots from forming while thrombolytics may be utilized to dissolve existing blood clots. However, not all patients can be treated with anticoagulants and/or thrombolytics. Therefore, in some instances, medical devices may be utilized to mechanically extract (e.g., aspirate) a volume of thrombus via a catheter-based intervention. For example, a catheter coupled to a large-bore aspiration device (e.g., syringe) may be utilized to aspirate thrombus. Accordingly, it can be appreciated that the syringe may be designed to create maximum vacuum power sufficient to dislodge and extract the thrombus through the catheter lumen. Large-bore aspiration devices designed to maximize vacuum power through an aspiration catheter are disclosed herein.

FIG. 1 is a side view of an example large bore vacuum source 10 (e.g., syringe). It can be appreciated that the syringe 10 may include both a barrel component 12 having a lumen (e.g., chamber) within which a plunger 18 (e.g., piston) may be positioned. The barrel 12 of the syringe 10 may include a distal end region 14 and a proximal end region 16. In some instances, the proximal end region of the barrel 12 may include one of more finger flanges 11 (e.g., finger grips) extending radially away from the outer surface of barrel 12. Similarly, the proximal end of the plunger may include a plunger flange 13 designed to permit a clinician to advance and/or retract the plunger 18 within the lumen of the barrel 12. It can be appreciated that a clinician may utilize the one or more finger flanges 11 in conjunction with the plunger flange 13 to advance and/or retract the plunger 18 within the lumen of the barrel 12.

FIG. 1 illustrates the syringe 10 having the plunger 18 slidably and rotatably positioned within a lumen of the barrel 12. For clarity, the plunger 18 is illustrates as a dotted line within the lumen of the barrel 12. In some examples, it can be appreciated that the plunger 18, the barrel 12 or both the plunger 18 and the barrel 12 may be constructed from a transparent material which permits visualization of contents within the lumen of the barrel 12. For example, the plunger 18, the barrel 12 or both the plunger 18 and the barrel 12 may be constructed from a polymeric, transparent material which may permit the visualization of a blood clot after being aspirated into the lumen of the barrel 12.

Figure 3:
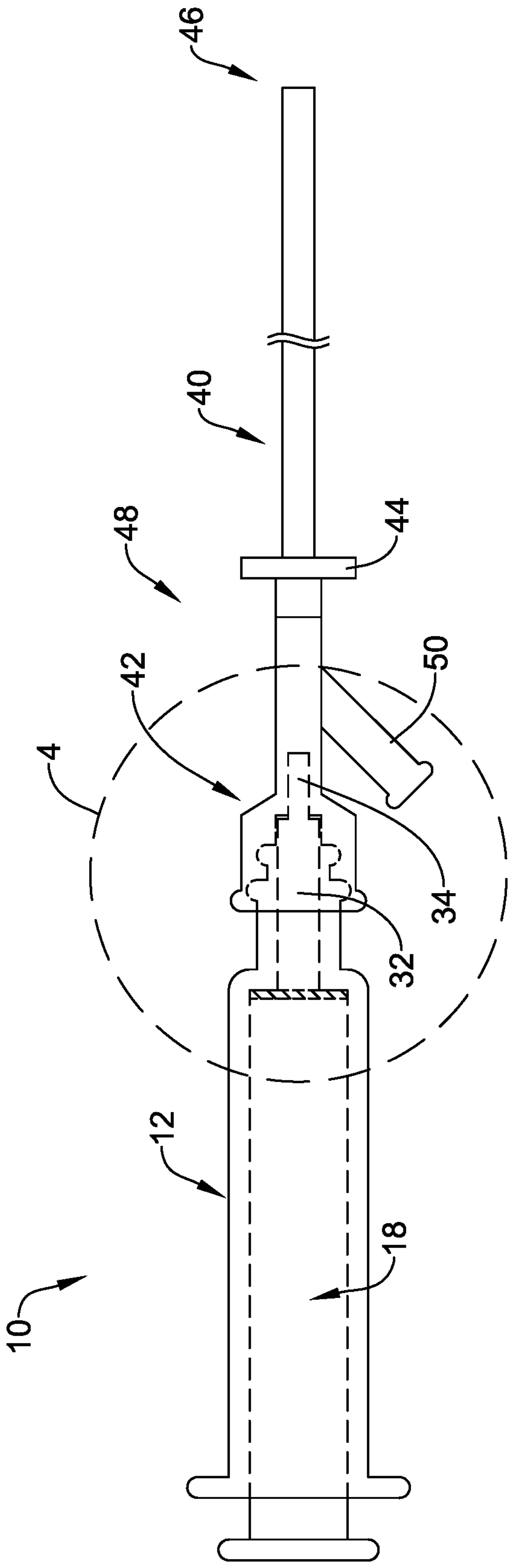
FIG. 3 illustrates an example aspiration system including a syringe coupled to an aspiration catheter.

Additionally, FIG. 1 illustrates that the distal end 14 of the barrel 12 may include one or more features designed to couple the barrel 12 of the syringe 10 to an aspiration catheter 48 (illustrated in FIG. 3). It can be appreciated that the distal end region 14 of the barrel 12 may include one or more features 24 which permit the distal end region 14 of the barrel 12 to be rotated (e.g., screwed) onto a manifold of an aspiration catheter. For example, it can be appreciated that the distal end region 14 of the barrel 12 may include a standard luer fitting (e.g., luer lock) that can be coupled to a manifold of an aspiration catheter.

As will be discussed in greater detail below, FIG. 1 further illustrates that, in some examples, the plunger 18 may include a body portion 28 (shown in FIG. 2) and a distal tip 27 (shown in FIG. 2) extending distally away from the body portion 28. As shown in FIG. 1, when the plunger 18 is fully advanced into the lumen (e.g., chamber) of the barrel 12, a portion of the distal tip 27 may extend distally of the end 19 of the barrel 12. For example, FIG. 1 illustrates the end 21 of the distal tip 27 extending distally of the end 19 of the distal end region 14 of the barrel 12. As will be discussed in greater detail below, the portion of the distal tip 27 extending beyond the end 19 of the barrel 12 may extend into a manifold of an aspiration catheter.

Figure 2:
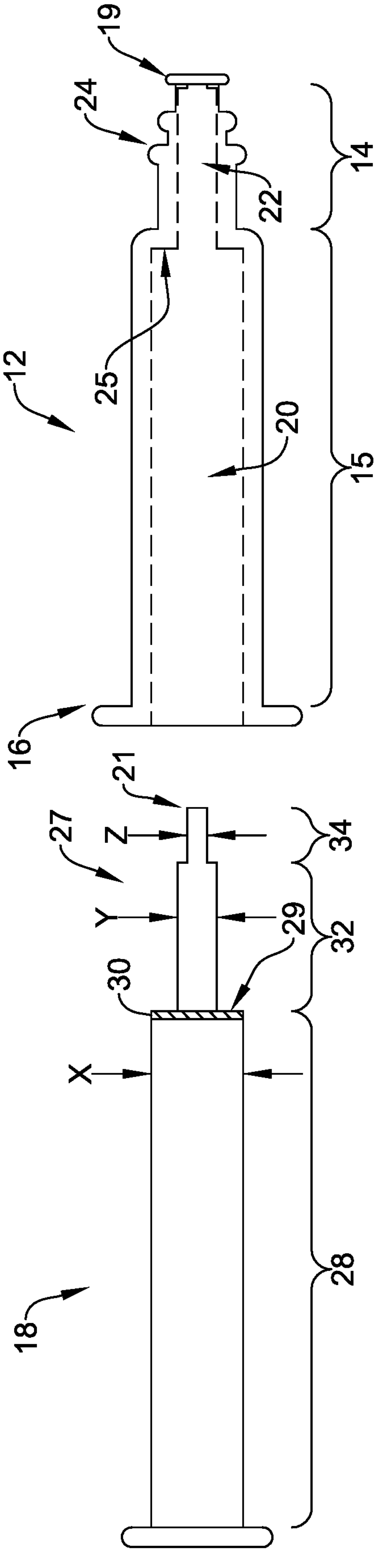
FIG. 2 illustrates the plunger and barrel of the syringe shown in FIG. 1.

FIG. 2 illustrates the barrel 12 spaced away from the plunger 18 of the syringe 10 described above. It can be appreciated that FIG. 2 illustrates that plunger 18 after having been fully retracted and removed from the lumen 20 of the barrel 12. FIG. 2 further illustrates that the plunger 18 may include a body portion 28 extending distally from the plunger flange 13. In some examples, the cross-sectional shape of the body portion of the is plunger 18 may be substantially cylindrical. However, in other examples, the cross-sectional shape of the body portion 28 of the plunger 18 may include other shapes, including ovular, triangular, square, rectangular, star-shaped, polygonal or other similar shapes.

FIG. 2 further illustrates that the plunger 12 may include a stopper (e.g., gasket) 30 positioned adjacent the distal end of the body portion 28. In some examples, the stopper 30 may include a cap which covers all or a portion of the distal end of the body portion 28. However, in other examples, the stopper 30 may include an O-ring which extends circumferentially around the outer surface of the body portion 28 of the plunger 18. For example, the stopper 30 may include an O-ring which is nested in a circumferential groove formed in the outer surface of the body portion 28 of the plunger 18.

It can be appreciated that the stopper 30 of the syringe 10 may be designed to seal against an inner surface of the of the barrel 12. For example, as illustrated in FIG. 2, the barrel 12 may include an inner surface which defines a first lumen 20 and a second lumen 22. It can be appreciated that the stopper 30 may be designed to seal against the inner surface of the barrel 12 which defines the first lumen 20 of the barrel 12. Additionally, it can be further appreciated that the seal provided by the stopper 30 against the inner surface of the barrel permits the plunger 18 to generate a vacuum force when retracted in a distal-to-proximal direction relative to the barrel 12.

FIG. 2 further illustrates that the plunger 18 may further include a distal tip portion 27 extending distally from the distal end of the body portion 18. The distal tip portion 27 may include a first tip portion 32 and a second tip portion 34. As illustrated in FIG. 2, the second tip portion 34 may extend distally from the first tip portion 34.

FIG. 2 illustrates that the body portion 28 may include an outer diameter "X", the first tip portion may include an outer diameter "Y" and the second tip portion may include an outer diameter "Z." In some examples, the outer diameter X may be about 0.25 inches to about 2 inches, or about 0.75 inches to about 1.5 inches, or about 0.90 inches to about 1.1 inches, or about 1.0 inch. Further, in some examples, the outer diameter Y may be about 0.10 inches to about 0.75 inches, or about 0.15 inches to about 0.5 inches, or about 0.20 inches to about 0.35 inches, or about 0.26 inches. Further yet, in some examples, the outer diameter Z may be about 0.10 inches to about 0.75 inches, or about 0.15 inches to about 0.5 inches, or about 0.20 inches to about 0.35 inches, or about 0.22 inches. It can be appreciated that, in some examples the outer diameter X of the body portion 28 may be larger than the outer diameter Y and outer diameter Z of the first tip portion 32 and the second tip portion 34, respectively. Further, in some examples (such as that illustrated in FIG. 2), the outer diameter Y of the first tip portion 32 may be larger than the outer diameter Z of the second tip portion 34. In yet other examples, it can be appreciated that the outer diameter X of the body portion may be 1.25, 1.5, 1.75, 2, 3, 4, 5, 6, 7, 8 or more times larger than the outer diameter Y of the first tip portion 32. For example, the ratio of the outer diameter X to the outer diameter Y may be about 3:2, or about 2:1, or about 3:1, or about 4:1.

FIG. 2 further illustrates that the body portion 28 may include a first length measured along the longitudinal axis of the plunger 18, the first tip portion 32 may include a second length measured along the longitudinal axis of the plunger 18 and the third tip portion 34 may include a third length measured along the longitudinal axis of the plunger 18. In some examples, the length of the first tip portion 32 may be larger than the diameter X of the body portion 28. Additionally, in some examples, the length of the first tip portion 32 may be about 1.25 times longer than the third tip portion 34, about 1.5 times longer than the third tip portion 34, about twice as long as the third tip portion 34, about three times as long as the third tip portion 34, about four times as long as the third tip portion 34, or about five times as long as the third tip portion 34.

As discussed above, FIG. 2 illustrates that the barrel 12 may include a first lumen 20 and a second lumen 22. It can be appreciated the diameter of the first lumen 20 may be sized to accept the body portion 28 of the plunger 18, while the second lumen 22 may be sized to accept the first tip portion 32 of the distal tip portion 27. In other words, the first lumen 20 and the second lumen 22 together may define an inner lumen profile that matches the outer surface profile of the body portion 28 and the first tip portion 32 of the distal tip portion 27. Additionally, FIG. 2 illustrates that the inner surface of the barrel 12 may further define a proximal-facing surface 25, extending circumferentially around the longitudinal axis of the barrel 18. It can be appreciated that the plunger 18 may be inserted into the lumen 20 of the barrel 12 and advanced distally to a position in which a is distal-facing surface 29 of the plunger 18 engages the proximal-facing surface 25 of the barrel 12. In other words, the plunger 18 may be advanced in a distal-to-proximal direction to a position in which the proximal-facing surface 25 acts as a positive stop and engages the distal-facing surface 29 of the plunger 18.

Referring to FIG. 1 and FIG. 2, it can be appreciated that when the plunger 18 is advanced within the lumen 20 to a position in which the distal-facing surface 29 of the plunger 18 engages the proximal-facing surface 25 of the barrel 12, the distal tip portion 27 may be advanced within the lumen 22 of the barrel 12. It can be further appreciated that as the plunger 18 is advanced within the lumen 20, the distal tip portion 27 may be advanced within the lumen 22 such that a portion of the second tip portion 34 extends distally past the end 19 of the barrel 12. Referring back to FIG. 1, as the plunger 18 is advanced within the lumen 20 to a position in which the distal-facing surface 29 of the plunger 18 engages the proximal-facing surface 25 of the barrel 12, a portion of the second tip portion 34 extends distally past the end 19 of the barrel 12. FIG. 1 illustrates the end 21 of the second tip portion 34 extending distally past the end 19 of the distal end region 14 of the barrel 12.

FIG. 3 illustrates the syringe 10 coupled to an aspiration catheter 48. The aspiration catheter 48 shown in FIG. 3 may include a manifold 42 attached to a tubular member 40. The tubular member 40 may include a distal end 46 located opposite the manifold 42. The tubular member 40 may include an inner diameter approximately 18 to 26 French.

FIG. 3 further illustrates the distal end region of the barrel 12 may be connected to a manifold 42 of the aspiration catheter 48. As described above, in some examples, the distal end region of the barrel 12 of the syringe 10 may include one or more features which rotationally engage with mating features of the manifold 42. For example, the distal end region of the barrel 12 may include a luer lock connector which is designed to engage and connect with the manifold 42.

As described above, FIG. 3 illustrates the plunger 18 positioned within the barrel 12 such that the first tip portion 32 has been advanced within the lumen 22 of the barrel such that the first tip portion 32 has filled the entire space of the lumen 22. In other is words, the plunger 18 has been advanced within the barrel 12 such that the first tip portion 32 has replaced any fluid (e.g., saline, blood, water, etc.) that may have been present in the lumen 22 of the barrel 12. Additionally, FIG. 3 further illustrates that the plunger 18 has been advanced within the barrel 12 such that the second tip portion 32 has been advanced out of the end of the barrel 12 (e.g., distally past the end of the barrel 12) and into a lumen of the manifold 42. In other words, the second tip portion 32 has been advanced distally out of the barrel 12 whereby it fills space defined by a lumen of the manifold 42. It can be appreciated that the lumens 20/22 of the barrel may be in fluid communication with the lumen of the manifold.

Additionally, FIG. 3 illustrates that the aspiration catheter 48 may include a clamp 44 positioned along the tubular member 40. The clamp 40 may be utilized to control flow through the tubular member 40. For example, the syringe 10 may be utilized to create a vacuum pressure proximal to the clamp 40. At a clinician's discretion, the clamp 44 may be opened whereby the vacuum pressure generated by the syringe 10 may create a vacuum force (e.g., suction) through the tubular member 40. It can be appreciated that the vacuum force generated through the tubular member 40 may aspirate blood clots or thrombus material located adjacent the distal end 46 of the tubular member 40.

Figure 4:
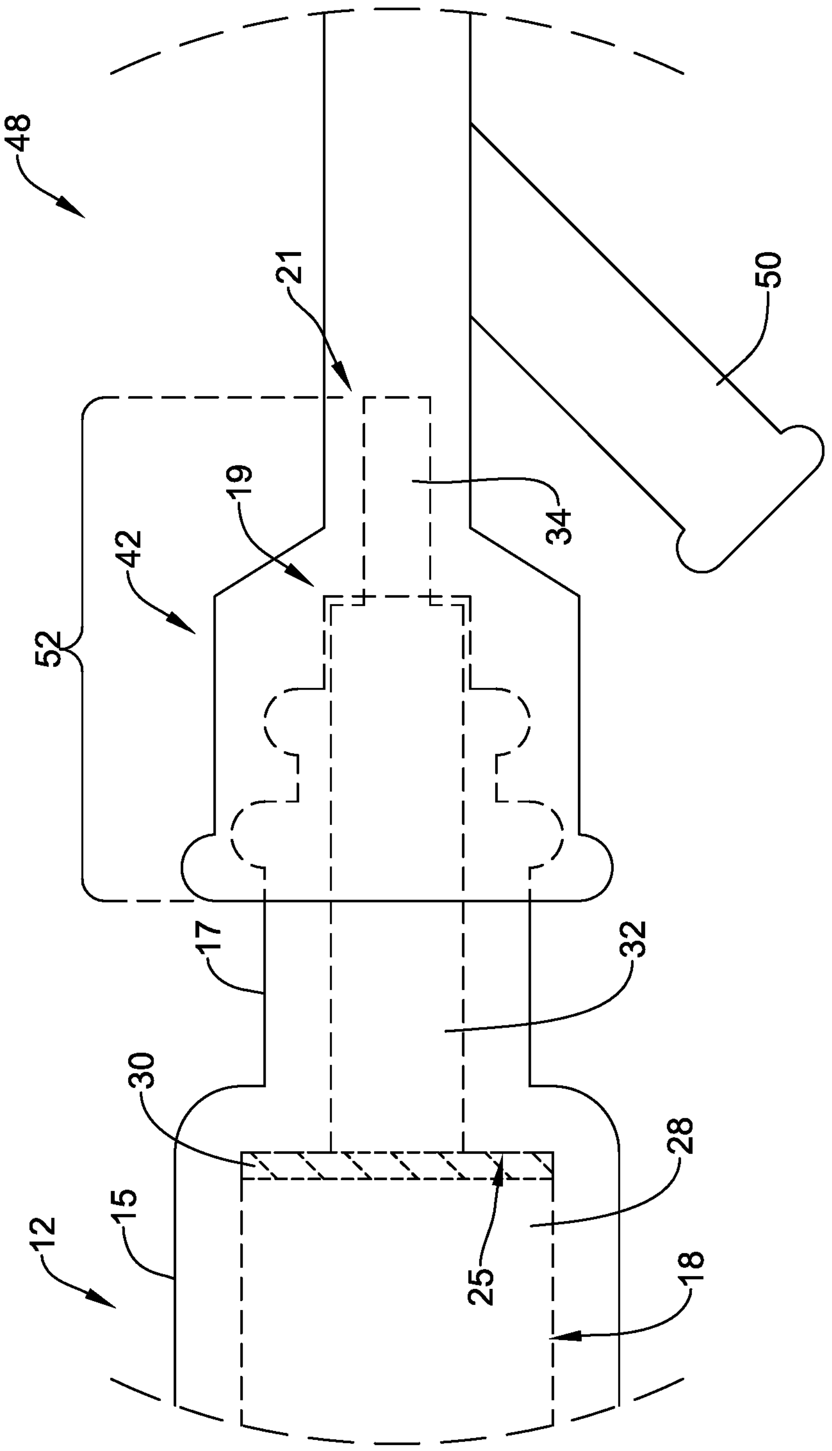
FIG. 4 illustrates a cross-section of a portion of the aspiration system illustrated in FIG. 3.

FIG. 4 illustrates a detailed view of a portion of the syringe 10 connected to the aspiration catheter 48 shown in FIG. 3. FIG. 4 illustrates the barrel 12 connected to the manifold 42 as described above. Further, FIG. 4 illustrates that the plunger 18 has been advanced distally within the lumen 20 of the barrel 12 to a position in which the stopper 30 has engaged the proximal-facing surface 25 of the barrel 12. Accordingly, the first portion 32 of the distal tip portion 27 has been advanced within lumen 22 of the barrel 12 such that it fills the entire space of the lumen 22. Additionally, FIG. 4 illustrates the second tip portion 34 extending distally past the end 19 of the distal end region 14 of the barrel 12 such that it fills space define by a lumen of the manifold 42. FIG. 4 illustrates that together the first portion 32 and the second tip portion 34 have advanced into the manifold 42 of the aspiration catheter a distance identified by the reference numeral 52.

It can be appreciated that the catheter aspiration system (including the syringe 10 and the aspiration catheter 48) shown in FIGS. 3-4 may be utilized to remove blood clots from a blood vessel. For example, the catheter aspiration system (including the syringe 10 and the aspiration catheter 48) shown in FIGS. 3-4 may be utilized to generate suction forces for aspirating clot material from within a blood vessel. It can be appreciated that generating maximum suction forces to aspirate clot material may require air to be purged from the barrel 12, the manifold 42 and the tubular member 40. Accordingly, prior to attaching the syringe 10 to the manifold 42 as described above, a clinician may initially "prep" the aspiration catheter 48 such that both the manifold 42 and the tubular member 40 are full of fluid (e.g., saline). Additionally, the clinician may initially "prep" the syringe 10 such that plunger 18 is fully seated with the lumens 20/22 of the barrel, thus removing all air from the lumens 20/22 of the barrel 12. Next, the clinician may attach the distal end region 14 of the barrel 12 to the manifold 42.

However, as described above, it can be appreciated that a portion of the second tip portion 34 may extend out of the barrel 12 as the clinician attaches the distal end region 14 of the barrel 12 to the manifold 42. Accordingly, the second tip portion 34 may replace and/or purge any air which may be present in the distal end of the lumen of the manifold 42. Accordingly, because the second tip portion 34 extends into the lumen of the manifold 42, it may assure that a continuous column of fluid extends from the distal end 19 of the barrel (or the end 21 of the distal tip portion 27) to the distal end 46 of the tubular member 40. This solid column of fluid assures a maximum vacuum force as the clinician retracts the plunger 18 to aspirate clot material positioned adjacent the distal end 46 of the aspiration catheter 48.

As described above, in some instances the clinician may utilize the clamp 44 to control initiation of the vacuum force generated by the syringe 10. For example, the clinician may prep the syringe 10 and the aspiration catheter 48 as described above, however, prior to retracting the plunger 18 to generate the vacuum force, the clinician may close the clamp 40. After closing the clamp 44, the clinician may retract the plunger 18 relative to the barrel 12, thereby generating vacuum forces within the barrel 12, the manifold and a portion of the tubular member 40. Further, after positioning the distal end 46 of the tubular member 40 in the desired location adjacent the blood clot, the clinician my open the clamp 44, thereby transferring the generated vacuum force to the distal end 46 of the tubular member 40. Further, it can be appreciated that the clinician may control the volume of the vacuum by withdrawing the plunger 18 more or less to provide a is desired amount of suction (e.g., aspiration) upon opening of the clamp 44.

Additionally, in another example technique, a clinician may bury the distal end 46 of the tubular member 40 in the clot material prior to retracting and generating a vacuum forces to aspirate the clot. For example, a clinician may prep and connect the syringe 10 to the aspiration catheter 48 as described above such that a continuous column of fluid extends from the distal end 19 of the barrel (or the end 21 of the distal tip portion 27) to the distal end 46 of the tubular member 40. Further, the clinician may advance the catheter within a blood vessel such that the distal end 46 of the tubular member 40 is adjacent a target clot material. The clinician may then bury the distal end 46 of the tubular member 40 into the clot material. Next, the clinician may retract the plunger 18 relative to the barrel 12, thereby generating a vacuum force in the tubular member 40. The vacuum force builds until it is strong enough to embolize and aspirate the thrombus. This technique can be repeated until the entire vacuum capacity of the syringe is used.

The materials that can be used for the various components of the medical device 10 and the various other medical devices disclosed herein may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), is polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 and the various other medical devices disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 and the various other medical devices disclosed herein in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 and the various other medical devices disclosed herein to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A syringe, comprising:

a barrel having a distal end region and an inner surface defining a lumen, wherein the inner surface includes a proximally facing surface, and wherein the distal end region includes a distal end; and a plunger having a body portion and a distal tip extending distally away from a distal end region of the body portion, wherein the distal end region includes a distally facing surface;

wherein the plunger is configured to be positioned within the lumen of the barrel;

wherein a portion of the distal tip of the plunger extends distally of the distal end of the barrel when the distally facing surface is engaged with the proximally facing surface;

wherein the distal end region of the body portion further includes a stopper, and where the stopper is configured to seal against the inner surface of the barrel.

2. The syringe of claim 1, wherein the distal end region of the barrel is configured to couple to a manifold of a catheter system, and wherein a portion of the distal tip of the plunger is configured to extend into a lumen of the manifold when the barrel is coupled to the manifold.

3. The syringe of claim 2, wherein the portion of the distal tip extending into the manifold is configured to purge air from the lumen of the manifold.

4. The syringe of claim 1, wherein the body portion of the plunger includes a first outer diameter, and wherein the distal tip of the plunger includes a second outer diameter smaller than the first outer diameter.

5. The syringe of claim 4, wherein the distal tip of the plunger further includes a first tip portion and a second tip portion, wherein the first tip portion includes the second outer diameter, and wherein the second tip portion includes a third outer diameter smaller than the second outer diameter.

6. The syringe of claim 5, wherein the first outer diameter of the plunger is about three times as large as the second outer diameter of the first tip portion.

7. The syringe of claim 6, wherein the second tip portion is positioned distal to the first tip portion.

8. The syringe of claim 5, wherein the first tip portion includes a first length, and wherein the second tip portion includes a second length, and wherein the first length is about twice as long as the second length.

9. The syringe of claim 8, wherein the first length of the first tip portion is longer than the first outer diameter of the body of the plunger.

* * * * *